United States Patent [19]

Cottman

[11] E Patent Number: Re. 32,618

[45] Reissued Date of Patent: Mar. 1, 1988

[54] MERCAPTOPHENOL DERIVATIVES AS AGE RESISTERS FOR POLYMERS

[75] Inventor: Kirkwood S. Cottman, Akron, Ohio

[73] Assignee: The Goodyear Tire & Rubber Company, Akron, Ohio

[21] Appl. No.: 853,820

[22] Filed: Apr. 18, 1986

Related U.S. Patent Documents

Reissue of:

[64] Patent No.: 4,308,199
Issued: Dec. 29, 1981
Appl. No.: 112,996
Filed: Jan. 17, 1980

[51] Int. Cl.[4] ..... C07C 149/36; C08K 5/36

[52] U.S. Cl. ..... 524/331; 568/47; 568/48; 568/53

[58] Field of Search ..... 524/331

[56] References Cited

U.S. PATENT DOCUMENTS

| | | | |
|---|---|---|---|
| 3,282,979 | 11/1966 | Reifschneider et al. | 568/53 |
| 3,305,522 | 2/1967 | Spacht | 260/815 |
| 3,484,804 | 1/1970 | O'Shea | 568/47 |
| 3,576,883 | 4/1971 | Neuworth | 568/48 |
| 3,708,883 | 1/1973 | Hickner et al. | 568/47 |
| 3,751,483 | 8/1973 | Cisney | 260/45.95 C |
| 3,897,500 | 7/1975 | Neuworth | 568/48 |
| 4,108,831 | 8/1978 | Cottman | 568/53 |
| 4,128,530 | 12/1978 | Cottman | 260/45.95 C |
| 4,143,076 | 3/1979 | Cottman | 568/53 |

OTHER PUBLICATIONS

A.C.S. Meeting, Div. Org. Coatings and Plastics Chemistry, 21, No. 2, (1961), pp. 79–107.

*Primary Examiner*—Veronica P. Hoke
*Attorney, Agent, or Firm*—D. O. Nickey

[57] ABSTRACT

Mercaptophenols are reacted with compounds containing olefinic unsaturation, or polycyclic olefins, or dihydroxy compounds to form phenolic antioxidants such as 3,8-bis(4-hydroxyphenylthio)-tricyclo[5.2.1.0.$^{2,6}$] decane; 1,4-bis[2-(4-hydroxyphenylthio)ethyl]benzene and age resistant polymers containing said antioxidants.

12 Claims, No Drawings

MERCAPTOPHENOL DERIVATIVES AS AGE RESISTERS FOR POLYMERS

Matter enclosed in heavy brackets [ ] appears in the original patent but forms no part of this reissue specification; matter printed in italics indicates the additions made by reissue.

TECHNICAL FIELD

This invention relates to age resisters for oxidizable organic materials, their preparation and use in the stabilization of polymers.

BACKGROUND ART

Polymers have proven to be some of the most difficult organic materials to stabilize against deleterious effects of oxygen and ozone, particularly unsaturated polymers, both natural and synthetic. Although many materials have been suggested and used as polymer stabilizers no completely satisfactory material has been found that will fully protect these polymers under the widely different conditions to which they are subjected.

Phenolic compounds have been among the more commonly used compounds that have found wide scale acceptance as polymer stabilizers. But many of the phenolic antioxidants, although reasonably effective stabilizers for organic materials, tend to impart discoloration and staining to the materials they are intended to stabilize.

In addition, some previously known phenolic antioxidants have limited solubility which causes difficulties in the incorporation of the antioxidant into the material which it is intended to protect.

U.S. Pat. No. 3,553,163 reveals alkylthio substituted mononuclear phenolic age resisters prepared by reacting an alkylthio phenol such as 2-methylthio phenol with an olefin type material such as 2-methyl-1-propene in the presence of a Friedel-Crafts type catalyst to yield compounds such as 2-tert.butyl-4-methylthio phenol.

U.S. Pat. No. 3,565,857 reveals alkylthio substituted polynuclear phenolic age resisters prepared by reacting in a one or two step process an alkylthio phenol such as 2-methylthio phenol with a condensation reactant such as an aldehyde or a ketone and subsequently reacting the product of the first reaction with a compound selected from the group consisting of olefins of 2 to 12 carbon atoms, cycloolefins containing from 5 to 9 carbon atoms and arylalkenes containing from 7 to 9 carbon atoms to produce antioxidant compounds such as 2,2'methylene bis(4-methylthio-6-tertiarybutyl phenol). U.S. Pat. No. 3,751,483 discloses phenolic thioethers wherein the sulfur atom on the phenolic nucleus is attached to an aliphatic, alicyclic or aralkyl group of 2 to 18 carbon atoms. These antioxidants are prepared by a reaction of metathesis wherein the phenolic substituents are incorporated through reaction with organic halides.

A variety of phenolic thioether compounds are known, wherein the sulfur atom on the phenolic nucleus is attached to a lower aralkyl, aliphatic or alicyclic group such as methyl, ethyl, cyclopropyl, propyl, isopropyl, benzyl or a corresponding alkenyl or alkynyl group. Such "lower" phenolic thioether compounds can be prepared, for example, by the method disclosed in U.S. Pat. No. 3,282,979 or by heating the corresponding hydroxyaryl sulfonium chlorides as taught in U.S. Pat. No. 3,133,971.

The search for new and better polymer stabilizers continues to command the attention of many skilled investigators, however, the prior art and literature on the subject does not disclose or suggest reacting polycyclic compounds containing one or more points of unsaturation or reacting monocyclic compounds containing one or more points of unsaturation with mercaptophenols. The process of the present invention and the novel compounds prepared therewith are excellent stabilizers that help overcome some of the prior art problems of stabilizer extraction, volatility and discoloration.

DISCLOSURE OF INVENTION

Stabilizers for polymeric materials which are subject to the deleterious effects of oxygen, ozone and sunlight, said stabilizers being phenolic compounds conforming to the following structural formulas I and II:

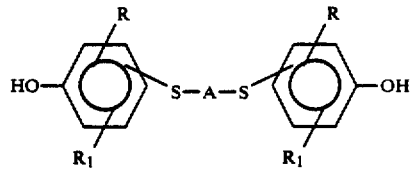

(I)

wherein R and $R_1$ are the same or different radicals selected from the group comprised of hydrogen, and aralkyl radicals of 7 to 9 carbon atoms, and wherein A is selected from the group comprised of divalent nonconjugated polycyclic radicals of 7 to 20 carbon atoms, or a radical of the formula:

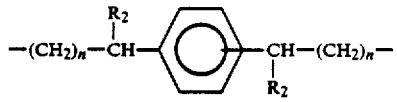

wherein n is 0 or 1 and $R_2$ is a hydrogen or methyl radical; or compounds of the structural Formula II:

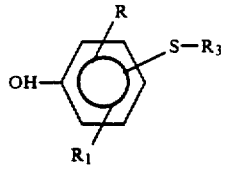

(II)

wherein R and $R_1$ are the same or different radicals selected from the group comprised of hydrogen radicals, and aralkyl radicals of 7 to 9 carbon atoms and $R_3$ is selected from the group comprised of saturated and unsaturated nonconjugated polycyclic radicals of 7 to 20 carbon atoms.

Examples of specific divalent radicals that conform to the radical A of structure (I) are:

3,8-tricyclo[5.2.1.$0^{2,6}$]decylene
3,9-tricyclo[5.2.1.$0^{2,6}$]decylene
4,8-tricyclo[5.2.1.$0^{2,6}$]decylene
4,9-tricyclo[5.2.1.$0^{2,6}$]decylene
5,11-pentacyclo[8.2.1.1.$^{4,7}$0.$^{2,9}$0.$^{3,8}$]tetradecylene
5,12-pentacyclo[8.2.1.1.$^{4,7}$0.$^{2,9}$0.$^{3,8}$]tetradecylene
2,5-bicyclo[2.2.1]heptylene
2,6-bicyclo[2.2.1]heptylene
1,4-phenylenedimethyl 2,2'-(1,4-phenylene)diethyl
2,2'-(1,4-phenylene)dipropyl Preferred compounds of the present invention are those which conform to the above structural formulae: I and II, wherein R and $R_1$ are hydrogen or Compounds of Structure I may be prepared by reacting preferably at least 2 moles of a mercaptophenol with one mole of a nonconjugated polycyclic diene such as Bicyclo[2.2.1]hepta-2,5-diene or a compound such as divinylbenzene. In both cases, the reaction may be carried out in the presence of free radical or acidic catalyst. Usually the reaction will occur without adding any catalyst. Examples of suitable acid catalysts are toluene sulfonic acid, sulfuric acid and $BF_3$. A free radical catalyst would be benzoyl peroxide. Ultraviolet light can also be used to catalyze the reactions.

Reactive alcohols such as $\alpha,\alpha'$-dihydroxyxylene may be reacted with mercaptophenols using acid catalyst to form compounds of Structure I.

Halides such as $\alpha,\alpha'$-dichloroxylene may be reacted with salts of mercaptophenols (4-hydroxy potassium phenylthiolate) to form compounds of Structure I.

Compounds of Structure II are prepared in the same manner as those of Structure I, except 1:1 adduct is formed due to functionality or reactive molar ratios.

The absence of a catalyst or the selection of a specific catalyst according to acidity or basicity can affect the isomeric configuration of the resulting compounds. For example, if an acidic catalyst such as toluene sulfonic acid is used when reacting divinyl-benzene with 4-mercaptophenol one skilled in the art would expect to form predominately 1,4-bis[1-(4-hydroxyphenylthio)ethyl]-benzene. In the same reaction if no catalyst or a free radical catalyst is used one would expect to form predominately 1,4-bis[2-(4-hydroxyphenylthio)ethyl]benzene.

Most of the stabilizers of the present invention are relatively soluble in polymers such as natural and synthetic rubber and have relatively low volatility and thus are less likely to leach out of the organic material they are intended to protect.

The following compounds illustrate but are not intended to limit the stabilizers of the present invention.

8-(4-hydroxyphenylthio)-tricyclo[5.2.1.0.$^{2,6}$]deca-3-ene
3,8-bis(4-hydroxyphenylthio)-tricyclo[5.2.1.0$^{2,6}$]decane
2-(4-hydroxyphenylthio)-bicyclo[2.2.1]hepta-5-ene
2,5-bis-(4-hydroxyphenylthio)-bicyclo[2.2.1]heptane
5,11-bis-(4-hydroxyphenylthio)-pentacyclo[8.2.1.1$^{4,7}$0.$^{2,9}$0$^{3,8}$]tetradecane
5-(4-hydroxyphenylthio)-pentacyclo[8.2.1.1$^{4,7}$0.$^{2,9}$0.$^{3,8}$-]tetradeca-11-ene
1,4-bis[2-(4-hydroxyphenylthio)ethyl]benzene
1,4-bis[1-(4-hydroxyphenylthio)ethyl]benzene
1-[2-(4-hydroxyphenylthio)ethyl]-4-[1-(4-hydroxyphenylthio)ethyl]benzene
2-(4-hydroxyphenylthio)-5-[2-(4-hydroxyphenylthio)ethyl]bicyclo[2.2.1]heptane
2-(4-hydroxyphenylthio)-5-vinyl bicyclo[2.2.1]heptane
1-(4-hydroxyphenylthio)-acenaphthene
(4-hydroxyphenylthio)-acenaphthene
2-(4-hydroxyphenylthio)-bicyclo[2.2.1]heptane
2-[3-(1-phenylethyl)-4-hydroxyphenylthio]bicyclo[2.2.1]heptane

BEST MODE FOR CARRYING OUT THE INVENTION

The following examples are provided to illustrate the preparation of compounds of this invention and not to limit the scope of this invention.

EXAMPLE 1

Preparation of 5,11-and/or -5,12-bis(3,5-ditertiary butyl-4-hydroxyphenylthio)pentacyclo[8.2.1.1.$^{4,7}$0.$^{2,9}$0.$^{3,8}$]tetradecane A reactor equipped with a thermometer, a water condenser and an agitator was charged with 64 grams (80% pure) of 2,6- ditertiary butyl-4-mercaptophenol and 19.4 grams of norbornadiene dimer dissolved in 150 ml. of benzene. Fifteen drops of $BF_3$ was added and the mixture was heated to 50° C. for 48 hours with agitation. The product was stripped under mild conditions to yield 85 grams with a melting point of 248°-252° C. after a methanol wash.

EXAMPLE 2

Preparation of 2,5 and/or 2,6-bis-(4-hydroxyphenylthio)bicyclo[2.2.1]heptane

To the reactor of Example 1 was added 66 grams of 4-mercaptophenol, 100 ml. toluene and 24.1 grams of 2,5-norbornadiene. The mixture was reached for 2.5 hours at 70° C. The mixture was cooled to ambient temperature and after 16 hours the white solid was filtered and washed with benzene. The product contained 17.9% sulfur and had a melting point of 142°-146° C.

EXAMPLE 3

Preparation of 8-(4-hydroxyphenylthio)-tricyclo[5.2.1.0$^{2,6}$]dec-3-ene

To the reactor vessel of Example 1 was added 51 grams of 4-mercaptophenol, 26.4 grams dicyclopentadiene and 70 ml. of benzene. The mixture was heated to 70° C. and 10 drops of toluenesulfonic acid was added and the reaction mixture was agitated 2 hours. The product was washed with water and then stripped to pot at 225° C. at 12 mm Hg, 51 grams of product was obtained with analysis indicating 12.5% sulfur compared to a theoretical value of 12.4% sulfur.

EXAMPLE 4

Preparation of 12 and/or 13-(4-hydroxyphenylthio)-pentacyclo[9.2.1.1$^{3,9}$,0.$^{2,10}$0$^{4,8}$]pentadeca-4-ene To the reactor of Example 1 was added 63 grams 4-marcaptophenol, 50 ml. benzene and 99 grams tricyclopentadiene. The mixture was heated to 40° C. and forty drops of $BF_3$ etherate was added. The mixture was reacted until the reactants disappeared by gas chromotography. The volatiles were stripped away and the yield was 100% of theoretical.

EXAMPLE 5

Preparation of 5,11 and/or 12-bis(4-hydroxyphenylthio)-pentacyclo-[8.2.1.$^{4,7}$0.$^{2,9}$0$^{3,8}$]tetradecane To the reactor of Example 1 was added 75 grams of 4-mercaptophenol, 100 ml toluene and 5 drops of $BF_3$ etherate. The mixture was heated to 50° C. and 46 grams of norbornadiene dimer was added over 30 minutes. The reaction mixture was agitated for 18 hours and then the product was stripped to pot at 160° C. and 2.3 mm Hg. The clear amber product weighed 109 grams with an analyzed sulfur content of 14.7% compared to theoretical sulfur content of 13.4%. Molecular weight was determined to be 435.

EXAMPLE 6

Preparation of 5-(4-hydroxyphenylthio)-pentacyclo[8.2.1.1$^{4,7}$0.$^{2,9}$0$^{3,8}$]tetradeca-11-ene.

To the reactor of Example 1 was added 50 ml. of toluene, 4 drops $BF_3$ etherate and 276 grams norbornadiene dimer. A solution of 63 grams 4-mercaptophenol dissolved in 150 ml. of toluene was added dropwise over a 1½ hour so as to keep the reaction mixture below 45° C. The mixture was reacted for 30 minutes and then 0.25 grams of $Na_2CO_3$ was added and the product stripped to a pot temperature of 185° C. at 15 mm. Hg. 159 grams of product was obtained.

EXAMPLE 7

Preparation of 4-hydroxyphenylthio cyclododecadiene

To the reactor of Example 1 was added 100.8 grams of 4-mercaptophenol and 100 ml toluene. While maintaining the reaction mixture at 40° C. 32.6 grams of 1,5,9-cyclododecatriene was added over a 20 minute period. The mixture was agitated for 24 hours and then stripped to a pot temperature of 220° C. and 11 mm. Hg. to yield 46 grams of product.

EXAMPLE 8

Preparation of 5-(4-hydroxyphenylthio)-pentacyclo[8.2.1.1.$^{4,7}$0.$^{2,9}$0.$^{3,8}$-]tetradeca-11-ene To the reactor of Example 1 was added two drops of $BF_3$ etherate, 100 ml. toluene and 292 grams 2,5-norbornadiene. While maintaining the reaction mixture temperature below at least 40° C., 100 grams 4-mercaptophenol dissolved in 100 ml. of toluene was added. The reaction mixture was agitated for one hour and then stripped in the presence of 2.0 grams of $Na_2CO_3$ to pot temperature of 130° C. at 30 mm Hg. for a yield of 181 grams.

EXAMPLE 9

To the reactor of Example 1 was added 126 grams of 4-mercaptophenol, 60 grams benzene and 2 grams toluenesulfonic acid and heated to 60° C. Then 61 grams of 72% divinylbenzene was added over a one hour period. The reaction product was reacted at 60° C. for one more hour and then neutralized with 4 grams $Na_2CO_3$ in aqueous solution. After decanting the product was stripped to pot 192° C. column 136° C. at 14 mm Hq. Weight 168 grams.

The polymers that may be conveniently protected by the compounds described herein are oxidizable vulcanized and unvulcanized polymers susceptible to oxidative degradation, such as natural rubber, balata, gutta percha and oxidizable synthetic polymers including those containing carbon to carbon double bonds, such as rubbery diene polymers, both conjugated and nonconjugated. Representative examples of the synthetic polymers used in the practice of this invention are polychloroprene; homopolymers of a conjugated 1,3-diene such as isoprene and butadiene, and in particular, polyisoprenes and polybutadienes having essentially all of their repeat units combined in a cis-1,4 structure; copolymers of a conjugated 1,3-diene such as isoprene and butadiene with up to 50 percent by weight of at least one copolymerizable monomer including ethylenically unsaturated monomers such as styrene and acrylonitrile; butyl rubber, which is a polymerization produce of a major proportion of a monoolefin and a minor proportion of a multiolefin such as a butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene and oils.

The phenolic antioxidants of this invention may be used with or without other stabilizers, vulcanizing agents, accelerators or other compounding ingredients. In order to effectively stabilize polymers, small proportions of one or more of the phenolic antioxidants in accordance with this invention are added to the polymer in a customary antioxidant amount which may vary somewhat depending upon the type and requirements of the polymers to be produced.

The method of addition of the antioxidant to the polymer is not critical. It may be added by any of the conventional means such as by adding to a polymer latex, milling on an open mill or by internal mixing. When the stabilizers of this invention are employed to stabilize the cis-1,4 polyisoprene or cis-1,4 polybutadiene rubbers, a convenient method of incorporation consists of adding the stabilizers to the inert organic solvent in which these polymers are normally prepared after the polymerization of the monomers is essentially complete.

Normally from about 0.001 part to about 5.0 parts of the antioxidant by weight based on the weight of the polymer can be used, although the precise amount of these effective stabilizers which is to be employed will depend somewhat on the nature of the polymer and the severity of the deteriorating conditions to which the polymer is to be exposed. It has been found that an effective antioxidant amount of the disclosed stabilizer in polymers will generally range from about 0.05 part to about 5.0 parts by weight or higher based on 100 parts by weight of the polymer although it is commonly preferred to use from about 0.5 part to about 2.0 parts by weight based on 100 parts by weight of the polymer in most instances where conjugated diene polymers are being stabilized. The above limits are merely guidelines.

In order to evaluate the effectiveness of the compounds of this invention as stabilizers for polymers representative compounds of this invention were incorporated into an oxidizable polymer.

Several of the products produced in the previous examples were evaluated in SBR 1006 by oxygen absorption at 100° C. Also evaluated were two SBR 1006 samples stabilized with two phenolic antioxidants not within the practice of the present invention. One part of the antioxidant was used in each experiment. The data are summarized below in Table I. The testing procedure is described in further detail in Industrial and Engineering Chemistry, 43, page 456 (1951) and Industrial and Engineering Chemistry, 45, page 392 (1953).

TABLE I $O_2$ Absorption of SBR 1006 With Antioxidants

| Antioxidant | Hours to Absorb 1.0% $O_2$ by Wt. |
|---|---|
| Wingstay L* | 341 |
| Example 3 | 793 |
| Example 4 | 587 |
| Example 5 | 670 |
| Example 6 | 713 |

TABLE I-continued

| $O_2$ Absorption of SBR 1006 With Antioxidants | |
|---|---|
| Antioxidant | Hours to Absorb 1.0% $O_2$ by Wt. |
| Example 7 | 577 |
| Wingstay L* | 356 |

*Wingstay L is the tradename for the butylated reaction product of p-cresol and dicyclopentadiene.

The results demonstrate the superior activity of the compounds of the present invention (Products of Example 3 through 7) as stabilizers for SBR.

Products from Examples 1, 2, 5 and 9 were also evaluated in SBR as stabilizers. Table II contains products from Examples 1, 2, 5 and 9 along with several other compounds that conform to this invention.

TABLE II

| Antioxidant | Hours to Absorb 1.0% $O_2$ |
|---|---|
| Example 1 | 397 |
| Example 2 | 1034 |
| 1,4-bis(2,6-ditertiary-4-hydroxyphenylthio)butane | 301 |
| Wingstay L* | 363 |
| Example 5 | 940 |
| 5,11 and/or 12[3,5(1-phenylethyl)-4-hydroxyphenylthio]pentacyclo[8.2.1.1.$^{4,7}$0.$^{2,9}$0.$^{3,8}$]tetradecane | 706 |
| Wingstay L* | 326 |
| Example 9 | 732 |
| Reaction product of isobutylene and and product of Example 10 | 852 |
| Wingstay L* | 341 |

*Wingstay L is the tradename for the butylated reaction product of p-cresol and dicyclopentadiene.

While certain representative embodiments and details have been shown for the purpose of illustrating the invention it will be apparent to those skilled in the art that various changes and modifications may be made therein without departing from the spirit or scope of the invention.

I claim:

1. A polymer subject to oxidative degradation having incorporated therein an antioxidant amount of a composition conforming to the following structural formula:

(I)

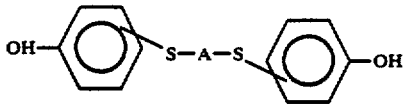

wherein A is selected from the group comprising divalent nonconjugated polycyclic radicals of 7 to 20 carbon atoms or a radical of the formula:

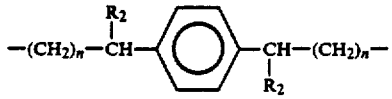

wherein n is 0 or 1 and $R_2$ is a hydrogen radical or a methyl radical.

2. A polymer according to claim 1 wherein the phenolic hydroxyl group is para to the sulfur atom.

3. A composition of matter according to claim [19] *8* wherein R and $R_1$ are hydrogen or [alkyl] *aralkyl* radicals of [1 to 4] *8 to 9* carbon atoms.

4. The polymer according to claim 1 wherein the antioxidant composition is selected from the group consisting of:

*(1)* [(1)]

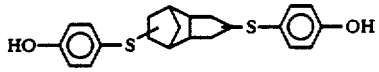

3.8 and/or 9 bis-(4-hydroxyphenylthio)bicyclo[5.2.1.0$^{2,6}$]decane

*(2)* [(2)]

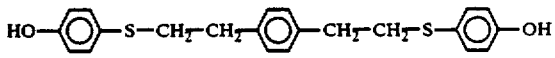

1,4-bis[2-(4-hydroxyphenylthio)ethyl]benzene

*(3)* [(3)]

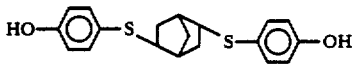

[(4)]

2,5-bis(4-hydroxyphenylthio)bicyclo[2.2.1]heptane

[5,11 and/or 12- 3,5-(1-phenylethyl)-4-hydroxyphenylthio pentacyclo[8.2.1$^{4,7}$0.$^{2,9}$0.$^{3,8}$]tetradecane]

5. A polymer subject to oxidative degradation having incorporated therein an antioxidant amount of a composition conforming to the following structural formula:

(II)

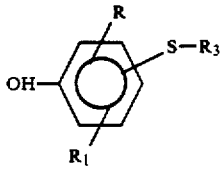

wherein R and $R_1$ are selected from the group comprised of hydrogen radicals and aralkyl radicals of 7 to 9 carbon atoms and $R_3$ is selected from the group comprised of saturated and unsaturated nonconjugated polycyclic radicals of 7 to 20 carbon atoms.

6. A polymer according to claim 5 wherein R and $R_1$ are located meta to the sulfur atom and the phenolic hydroxyl group is para to the sulfur atom.

7. A polymer according to claim 5 wherein the antioxidant composition is selected from the group consisting of 1. [8-(4-hydroxyphenylthio[5.2.1.0$^{3,6}$]deca-3-ene,] *8-(4-hydroxyphenylthio)-tricyclo[5.2.1.0$^{2,6}$]dec-3-ene,*
2. 2-(4-hydroxyphenylthio)bicyclo[2.2.1]hepta-5-ene,
3. 5-(4-hydroxyphenylthio)-pentacyclo[8.2.1.1.$^{4,7}$0.$^{2,9}$0.$^{3,8}$]tetradeca-11-ene.

8. A composition of matter conforming to the following structural formula:

(II)

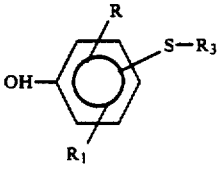

wherein R and $R_1$ are selected from the group comprised of hydrogen radicals and aralkyl radicals of 7 to 9 carbon atoms and $R_3$ is selected from the group comprised of saturated and unsaturated nonconjugated polycyclic radicals of 7 to 20 carbon atoms.

9. A composition of matter according to claim 8 wherein R and $R_1$ are located meta to the sulfur atom and the phenolic hydroxyl group is para to the sulfur atom.

10. A composition of matter conforming to the following structural formula:

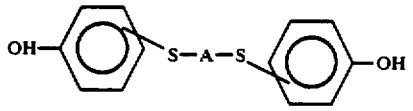

(I)

wherein A is selected from the group comprised of divalent nonconjugated polycyclic radicals of 7 to 20 carbon atoms or a radical of the formula:

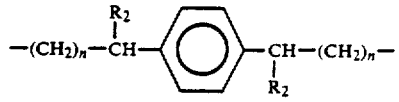

wherein n is 0 to 1 and $R_2$ is a hydrogen radical or a methyl radical.

11. A composition of matter according to claim 10 wherein the phenolic hydroxyl group is para to the sulfur atom.

*12. A polymer subject to oxidative degradation having incorporated therein an antioxidant amount of a composition selected from: 5,11 and/or -5,12-bis(3,5-ditertiary butyl-4-hydroxyphenylthio) pentacyclo[8.2.1.1.$^{4,7}$0.$^{2,9}$0.$^{3,8}$-]tetradecane.*

* * * * *